United States Patent [19]

Bontemps

[11] Patent Number: 5,695,764
[45] Date of Patent: Dec. 9, 1997

[54] MANUFACTURING AND PRESERVATION PROCEDURE FOR FRESH PLANT COSMETIC SUBSTANCES FREE OF PRESERVATIVE AND APPLIED IN THE FROZEN STATE

[76] Inventor: Raymond Bontemps, 15, rue Massenet, 75016 Paris, France

[21] Appl. No.: 618,788

[22] Filed: Mar. 20, 1996

Related U.S. Application Data

[63] Continuation of Ser. No. 381,949, filed as PCT/FR94/00703, Jun. 13, 1994, abandoned.

[30] Foreign Application Priority Data

Nov. 6, 1993 [FR] France .................. 93 07068

[51] Int. Cl.$^6$ ............................................. A61K 35/78
[52] U.S. Cl. .......................... 424/195.1; 424/401
[58] Field of Search ..................... 424/195.1, 401

[56] References Cited

FOREIGN PATENT DOCUMENTS

| 17595 | 10/1980 | European Pat. Off. | A61K 7/48 |
| 234143 | 9/1987 | European Pat. Off. | A61K 9/14 |
| 248753 | 12/1987 | European Pat. Off. | A23B 7/04 |
| 2539823 | 3/1977 | Germany | A61K 7/48 |
| 1303324 | 3/1993 | Germany | A61K 7/48 |

*Primary Examiner*—John W. Rollins
*Attorney, Agent, or Firm*—Antonelli, Terry, Stout & Kraus, LLP.

[57] ABSTRACT

Cosmetic products available in the form of frozen cakes obtained by rehydration of a lyophilizate with water or physiological serum, characterized in that the lyophilizate contains extracts of plant substances.

14 Claims, 1 Drawing Sheet

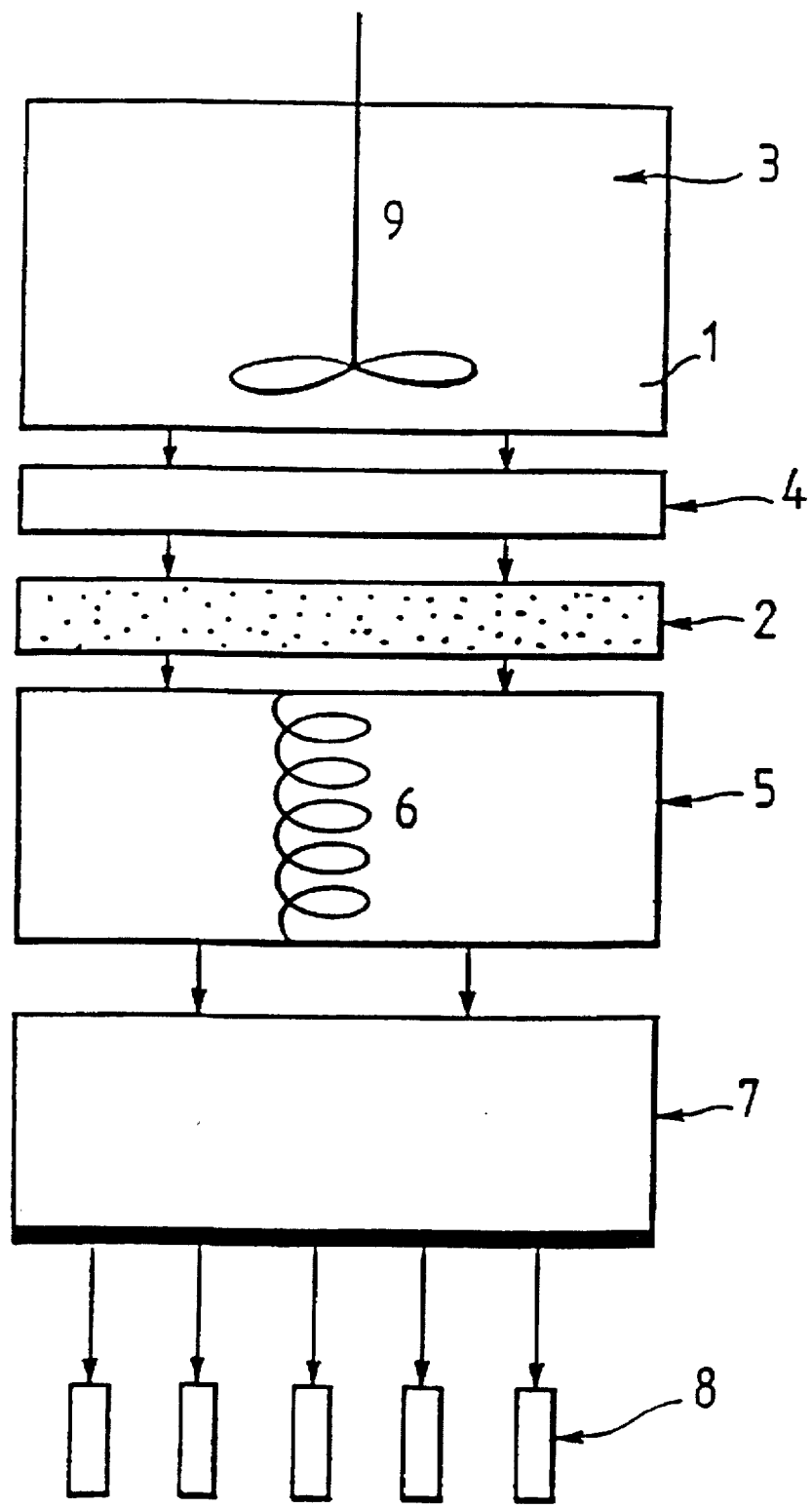
FIG_1

MANUFACTURING AND PRESERVATION PROCEDURE FOR FRESH PLANT COSMETIC SUBSTANCES FREE OF PRESERVATIVE AND APPLIED IN THE FROZEN STATE

This application is a Continuation of U.S. Ser. No. 08/381,949, filed as PCT/FR94/00703, Jun. 13, 1994, , now abandoned.

BACKGROUND OF THE INVENTION

The present invention relates to the preparation and preservation of cosmetic substances.

Hitherto in order to avoid introducing certain preservatives the vegetal and/or animal extracts were taken and cleaned, then stored in the form of a paste in Dry Ice. The hardened paste was converted at this temperature into short frozen sticks and directly applied at −20° C. to the skin which was massaged by means of the short stick.

Such products preserved in the form of frozen cakes based on substances of fetal or mesenchymal origin have been described in the European patent application No. 17595.

These procedures are difficult to apply for everyday usage. For example, after use the short stick must be stored in a freezer at −20° C. or in Dry Ice and its efficacy diminishes with time.

In addition, in certain cases the use of substances of animal origin is not suited either for reasons intrinsic to use or for regulatory reasons.

SUMMARY OF THE INVENTION

The present invention relates to a manufacturing and preservation procedure for cosmetic substances based on vegetal extracts particularly subject to air deterioration. These vegetal extracts are comparable to microceptors encountered in mesenchymal extracts of animal origin which are known to be particularly efficacious in the field of cosmetology when they are applied to the skin in the frozen state. In addition, their activity may be reinforced when the plants have themselves been enriched during culture in trace elements specific for the skin treated. Finally, their efficacy is the greater if the vegetal extracts are applied to the skin immediately after harvesting. At present additions of preservatives are used to maintain these vegetal extracts in satisfactory conditions of freshness. These preservatives are similar to those used for the cosmic products of vegetal origin of the mesenchymal type. These substances of fetal or plant origin are biogenic, i.e. specific cells (based on DNA or RNA) destined to create living matter. They must be applied to the skin and the dermis when in the fresh state, i.e. applied in situ after sampling or harvesting.

In order to use said substances a perfume and/or isotonic liquid is optionally incorporated such as physiological serum. A preservative is usually added to the mixture to assure its use for several days.

The present invention suggests an improvement which makes it possible to use fresh plants, which have optionally received a supplement of trace elements during their culture, while enhancing the efficacy of the procedure.

These trace elements are selected as a function of the specificity of the dermis of the patient.

Finally, in order to avoid the transport of the fresh plant extracts in Dry Ice, a paste is prepared with distilled water or with physiological serum starting from these cleaned and ground extracts. This paste is filtered, then lyophilized in order to obtain a dry extract. This dry extract is stored in plastic cases. When the user wishes to use the short stick of cosmetic he pours into the case a volume of water or physiological serum until a paste is obtained. The mixture is introduced into a freezer at −20°. Several hours after the user withdraws the case in order to extract the frozen stick which he uses for massage of the skin as has already been described elsewhere.

Finally, this procedure makes the cosmetic products available free of preservatives.

BRIEF DESCRIPTION OF THE DRAWINGS

FIG. 1 is a schematic flow chart of the method for preparing frozen cosmetic sticks.

DESCRIPTION OF THE PREFERRED EMBODIMENT

The invention called manufacturing and preservation procedure for fresh plant cosmetic substances free of preservative and applied in the frozen state is characterized by the grinding of plant extracts, optionally doped with traces elements during their culture.

The manufacturing procedure comprises the following steps:

a) grinding and mixing of a mixture containing at least plant extracts cleaned with distilled water or physiological serum, b) filtration of the paste obtained on a microporous filter, c) lyophilization or dehydration of the filtrate obtained, d) rehydration of the lyophilized or dehydrated extract and freezing of the paste obtained at about −200° C. prior to use.

The gelatinous magma obtained after grinding in step a) is filtered under pressure through a 0.2μ to 0.5μ micropore filter. The mixture is then lyophilized and placed in plastic cases in the form of short sticks. Immediately prior to use, the user adds a volume of several cubic centimeters of physiological serum to the case which he places in the freezer at −20° C. for several hours. It will subsequently be possible to take out the frozen stick and massage the epidermis.

The present invention will be better understood by reference to the schematic outline shown in FIG. 1 which presents the principle of the manufacturing procedure.

This Figure shows the extract storage vat containing plant extracts (1). This vat is maintained at a temperature of −20° C. The plant extracts are usually freshly harvested plants from a hydroponic medium (germinated wheat, cress, medicinal plants) which are doped with trace elements such as copper, zinc, manganese, etc. The doping with metal ions is obtained by immersing the roots in a dilute electrolyte containing the trace element metal ion and by applying an electric field between the roots and the leaves of the plant.

The vegetal extracts may also be fruit extracts, preferably acidic fruit extracts.

The plant extracts stored in the vat (1) are converted into a gelatinous mass by means of a mixer (9) which also acts as grinder. It is possible to make additions of physiological serum at level (3) in order to dilute the paste obtained.

This paste then passes over a preheater (4) which maintains the mixture at 0° C. At this temperature the gelatinous magma passes through a microporous filter (2) in order to remove all solid particles from it. The filtration through the micropores (2) is carried out under pressure and the pores of the filter have a diameter of from 0.2 to 0.5μ.

The paste thus prepared may be optionally collected in the reservoir (5) where it is stored at a temperature of −20° C. maintained by means of a pipe coil (6). When the paste has sufficient fluidity produced by means of additions of physiological serum it is lyophilized at level (7) in order to obtain a solid dehydrated compound. This solid compound is cut up into short sticks which are introduced into the cases which are crimped and rendered aseptic The entire case and contents are then stored at room temperature.

When it is desired to use these extracts it suffices to remove a case (8), add one volume of physiological serum and place the whole in a freezer.

When the paste contained in the case is frozen at −20° C. the short stick is extracted from the case to massage the skin.

The invention also relates to the cosmetic products available in the form of frozen cakes obtained by rehydration of a lyophilizate with water or physiological serum, characterized in that the lyophilizate contains extracts of plant substances.

The extracts of plant substances may be extracts of freshly harvested plants from a hydroponic medium (germinated wheat, cress, medicinal plants) and which are optionally doped previously with trace elements, in particular copper, zinc, or manganese, They may also be fruit extracts, preferably of acidic fruit.

They may finally be combined with other cosmetic extracts, in particular mesenchymal or fetal extracts of animal origin.

I claim:

1. A manufacturing and preservation procedure for fresh plant cosmetic substances free of preservative and applicable to the skin in a frozen state, comprising the following steps:
    a) grinding and mixing a mixture containing at least vegetal substances cleaned with distilled water or physiological serum to form a paste,
    b) filtering the paste obtained through a micropore filter to obtain a filtrate,
    c) lyophilizing or dehydrating the filtrate,
    d) rehydrating the lyophilized or dehydrated filtrate and freezing at −20° C. prior to use.

2. The procedure according to claim 1, wherein the filtering is carried out under pressure and the filter has a pore diameter between 0.2 and 0.5μ.

3. The procedure according to claim 1, wherein the vegetal substances are selected from fruit, vegetables, and plants harvested from hydroponic media.

4. The procedure according to claim 3, wherein the vegetal substances include germinated wheat, cress or medicinal plants.

5. The procedure according to claim 1, wherein the filtrate is refrigerated at about −20° C. prior to lyophilization.

6. The procedure according to claim 1, wherein a lyophilizate may be introduced into cases which are crimped and rendered aseptic.

7. The procedure according to claim 1, wherein the vegetal substances are recently harvested plants from hydroponic media which have been previously doped with trace elements.

8. The procedure according to claim 7, wherein the trace elements include copper, zinc or manganese.

9. A cosmetic product in the form of frozen cakes obtained by rehydration of a lyophilizate with water or physiological serum, wherein the lyophilizate contains extracts of vegetal substances.

10. The cosmetic product according to claim 9, wherein the vegetal substances are selected from fruit, vegetables, and plants harvested from hydroponic media.

11. The cosmetic product according to claim 10, wherein the vegetal substances include germinated wheat, cress or medicinal plants.

12. The cosmetic product according to claim 9, wherein the recently harvested plants in hydroponic media have been previously doped with trace elements.

13. The cosmetic product according to claim 12, wherein the trace elements include copper, zinc or manganese.

14. The cosmetic product according to claim 9, wherein the extracts of vegetal substances are further combined with mesenchymal or fetal extracts of animal origin.

* * * * *